United States Patent [19]
Norbeck et al.

[11] Patent Number: 6,037,157
[45] Date of Patent: *Mar. 14, 2000

[54] METHOD FOR IMPROVING PHARMACOKINETICS

[75] Inventors: Daniel W. Norbeck, Crystal Lake; Dale J. Kempf, Libertyville; John M. Leonard, Lake Bluff, all of Ill.; Richard J. Bertz, Kenosha, Wis.

[73] Assignee: Abbott Laboratories, Abbott Park, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/687,774

[22] Filed: Jun. 26, 1996

Related U.S. Application Data

[60] Provisional application No. 60/000,654, Jun. 29, 1995, and provisional application No. 60/003,849, Sep. 15, 1995.

[51] Int. Cl.[7] .............................. C12N 9/99; C07D 277/28
[52] U.S. Cl. .......................... 435/184; 548/204; 548/205; 514/365
[58] Field of Search ..................... 548/204, 205; 514/365; 435/184

[56] References Cited

U.S. PATENT DOCUMENTS

| | | | |
|---|---|---|---|
| 5,547,823 | 8/1996 | Tien et al. | 548/204 |
| 5,552,558 | 9/1996 | Kempf et al. | 549/552 |
| 5,674,882 | 10/1997 | Kempf et al. | 514/365 |
| 5,886,036 | 3/1999 | Kempf et al. | 514/533 |

FOREIGN PATENT DOCUMENTS

| | | |
|---|---|---|
| 0691345 | 1/1996 | European Pat. Off. . |
| 9511992 | 5/1995 | WIPO . |
| 9533464 | 12/1995 | WIPO . |
| 9604913 | 2/1996 | WIPO . |

OTHER PUBLICATIONS

S. Vella, Rationale and Experience with Reverse Transcriptase Inhibitors and Protease Inhibitors, Journ of Acquired Immune Def. Syndrome & Humane Retro. 10(Suppl. 1) S58–S61 1995.

J. Craig, et al., Int. Conf. AIDS 9(1993) PO–A25–0602 RO 31–8959, An Inhibitor of HIV Proteinase, Acts Beneficially with Other Antiviral Agents in 2– and 3–Way Combinations In Vitro.

D, Kempf, et al., 3rd Conf Retro and Opportun Infect (US) Jan. 28–Feb. 1, 1996 p. 79.

J. James, AIDS Treatment News, No. 231 Sep. 29, 1995.

*Primary Examiner*—John Kight
*Assistant Examiner*—Charanjit S. Aulakh
*Attorney, Agent, or Firm*—Steven R. Crowley

[57] ABSTRACT

A method is disclosed for improving the pharmacokinetics of a drug which is metabolized by cytochrome P450 monooxygenase.

18 Claims, No Drawings

METHOD FOR IMPROVING PHARMACOKINETICS

This application claims the benefit of U.S. Provisional Patent Application No. 60/000,654, filed Jun. 29, 1995 and also claims the benefit of U.S. Provisional Patent Application No. 60/003,849, filed Sep. 15, 1995, both of which are incorporated herein by reference.

TECHNICAL FIELD

The present invention relates to a novel composition and a method for improving the pharmacokinetics of drugs which are metabolized by cytochrome P450 monooxygenase. In addition, the present invention relates to a novel composition and a method for inhibiting retroviral proteases and in particular for inhibiting human immunodeficiency virus (HIV) protease and a composition and a method for inhibiting a retroviral infection, in particular an HIV infection

BACKGROUND OF THE INVENTION

Infection by the retrovirus known as human immunodeficiency virus (HIV) continues to be a serious human health problem. Methods for treating HIV infections include administering agents which inhibit the activity of viral enzymes which are essential to the life cycle of the virus.

The genomes of retroviruses encode a protease that is responsible for the proteolytic processing of one or more polyprotein precursors such as the pol and gag gene products. See Wellink, Arch. Virol. 98 1 (1988). Retroviral proteases most commonly process the gag precursor into core proteins, and also process the pol precursor into reverse transcriptase and retroviral protease. Retroviral proteases are known to be sequence specific. See Pearl, Nature 328 482 (1987).

The correct processing of the precursor polyproteins by the retroviral protease is necessary for the assembly of infectious virions. It has been shown that in vitro mutagenesis that produces protease-defective virus leads to the production of immature core forms which lack infectivity. See Crawford, J. Virol. 53 899 (1985); Katoh, et al., Virology 145 280 (1985). Therefore, retroviral protease inhibition provides an attractive target for antiviral therapy. See Mitsuya, Nature 325 775 (1987).

It has recently been disclosed that the HIV protease inhibitor ritonavir (also known as ABT-538) is effective in humans for inhibiting an HIV infection.

It has also been discovered that ritonavir is an inhibitor of the metabolic enzyme cytochrome P450 monooxygenase.

Some drugs and, in particular, some HIV protease inhibitors are metabolized by cytochrome P450 monooxygenase, leading to unfavorable pharmacokinetics and the need for more frequent and higher doses than are most desirable. Administration of such drugs with an agent that inhibits metabolism by cytochrome P450 monooxygenase will improve the pharmacokinetics (i.e., increase half-life, increase the time to peak plasma concentration, increase blood levels) of the drug.

It has been discovered that coadministration of ritonavir with a drug which is metabolized by cytochrome P450 monooxygenase, especially the P450 3A4 isozyme, causes an improvement in the pharmacokinetics of such a drug.

In particular, it has been discovered that coadministration of ritonavir with an HIV protease inhibitor which is metabolized by cytochrome P450 monooxygenase causes an unexpected improvement in the pharmacokinetics of such an HIV protease inhibitor.

DISCLOSURE OF THE INVENTION

In accordance with the present invention, there is disclosed a method of improving the pharmacokinetics of a drug (or a pharmaceutically acceptable salt thereof) which is metabolized by cytochrome P450 monooxygenase comprising coadministering ritonavir or a pharmaceutically acceptable salt thereof. When administered in combination, the two therapeutic agents can be formulated as separate compositions which are administered at the same time or different times, or the two therapeutic agents can be administered as a single composition.

Drugs which are metabolized by cytochrome P450 monooxygenase and which benefit from coadministration with ritonavir include the immunosuppressants cyclosporine, FK-506 and rapamycin, the chemotherapeutic agents taxol and taxotere, the antibiotic clarithromycin and the HIV protease inhibitors A-77003, A-80987, MK-639, saquinavir, VX-478, AG1343, DMP-323, XM-450, BILA 2011 BS, BILA 1096 BS, BILA 2185 BS, BMS 186,318, LB71262, SC-52151, SC-629 (N,N-dimethylglycyl-N-(2-hyrdoxy-3-(((4-methoxyphenyl)sulphonyl)(2-methylpropyl)amino)-1-(phenylmethyl)propyl)-3-methyl-L-valinamide), KNI-272, CGP 53437, CGP 57813 and U-103017.

In a preferred embodiment of the present invention, there is disclosed a method for improving the pharmacokinetics of an HIV protease inhibitor (or a pharmaceutically acceptable salt thereof) which is metabolized by cytochrome P450 monooxygenase comprising coadministering ritonavir or a pharmaceutically acceptable salt thereof. Such a combination of ritonavir or a pharmaceutically acceptable salt thereof and an HIV protease inhibitor or a pharmaceutically acceptable salt thereof which is metabolized by cytochrome P450 monooxygenase is useful for inhibiting HIV protease in humans and is also useful for inhibition, treatment or prophylaxis of an HIV infection or AIDS (acquired immune deficiency syndrome) in humans. When administered in combination, the two therapeutic agents can be formulated as separate compositions which are administered at the same time or different times, or the two therapeutic agents can be administered as a single composition.

Preferred HIV protease inhibitors which are metabolized by cytochrome P450 monooxygenase include A-77003, A-80987, MK-639, saquinavir, VX-478 and AG1343.

Ritonavir is (2S,3S,5S)-5-(N-(N-((N-Methyl-N-((2-isopropyl-4-thiazolyl)methyl)amino)carbonyl)-L-valinyl) amino)-2-(N-((5-thiazolyl)methoxycarbonyl)amino)-1,6-diphenyl-3-hydroxyhexane or a pharmaceutically acceptable salt thereof. Ritonavir can be synthesized by the procedures disclosed in PCT Patent Application No. WO94/14436, published Jul. 7, 1994, and the U.S. patent application Ser. No. 08/469,965, filed Jun. 6, 1995, both of which are incorporated herein by reference.

VX-478 is

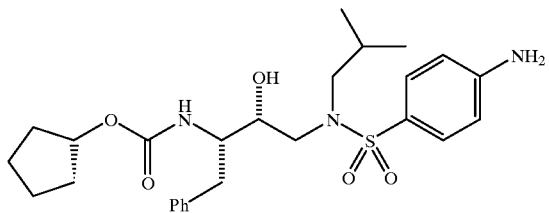

or a pharmaceutically acceptable salt thereof. VX-478 can by synthesized by the procedures disclosed in PCT Patent Application No. WO94/05639, published Mar. 17, 1994, which is incorporated herein by reference.

A-77003 is (2S,3R,4S,5S)-2,5-Di-(N-((N-methyl)-N-((2-pyridinyl)methyl)amino)carbonylvalinylamino)-3,4-dihydroxy-1,6-diphenyl hexane or a pharmaceutically acceptable salt thereof and is disclosed in U.S. Pat. No. 5,142,056, issued Aug. 25, 1992, which is incorporated herein by reference.

A-80987 is (2S,3S,5S)-2-(N-(N-((2-Pyridinyl)methoxycarbonyl)valinyl)-amino)-5-(N-(3-pyridinyl)methoxycarbonyl)amino)-1,6-diphenyl-3-hydroxyhexane or a pharmaceutically acceptable salt thereof and is disclosed in U.S. Pat. No. 5,354,866, issued Oct. 11, 1994, which is incorporated herein by reference.

MK-639 is N-(2(R)-hydroxy-1(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide or a pharmaceutically acceptable salt thereof and is disclosed in European Patent Application No. EP541168, published May 12, 1993 and U.S. Pat. No. 5,413,999, issued May 9, 1995, both of which are incorporated herein by reference.

Saquinavir is N-tert-butyl-decahydro-2-[2(R)-hydroxy-4-phenyl-3(S)-[[N-(2-quinolylcarbonyl)-L-asparaginyl]amino]butyl]-(4aS,8aS)-isoquinoline-3(S)-carboxamide or a pharmaceutically acceptable salt thereof and is disclosed in U.S. Pat. No. 5,196,438, issued Mar. 23, 1993, which is incorporated herein by reference.

AG1343 is

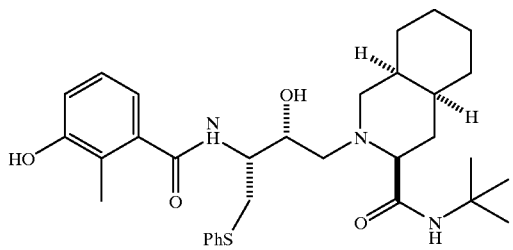

or a pharmaceutically acceptable salt thereof and is disclosed in PCT Patent Application No. WO95/09843, published Apr. 13, 1995 and U.S. Pat. No. 5,484,926, issued Jan. 16, 1996, both of which are incorporated herein by reference.

DMP-323 is

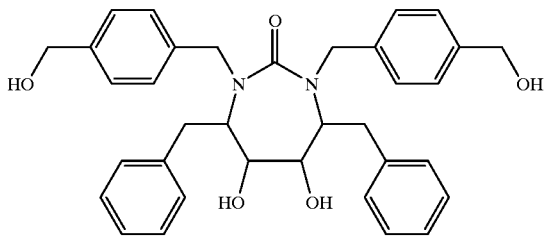

or a pharmaceutically acceptable salt thereof and is disclosed in PCT Patent Application No. WO93/07128, published Apr. 15, 1993, which is incorporated herein by reference.

XM-450 is

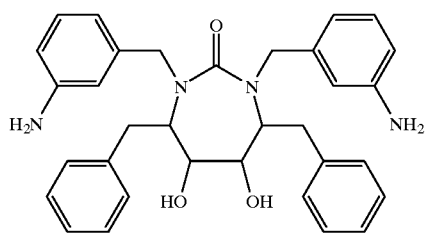

or a pharmaceutically acceptable salt thereof and is disclosed in PCT Patent Application No. WO93/07128, published Apr. 15, 1993, which is incorporated herein by reference.

BILA 2011 is

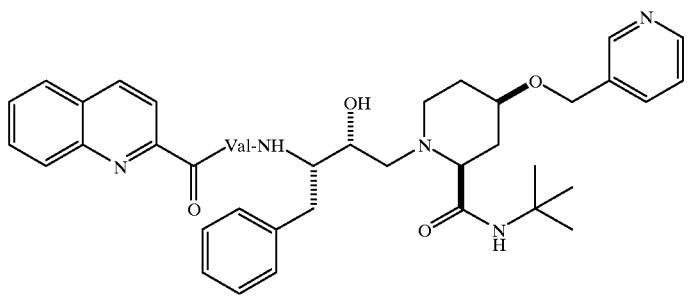

or a pharmaceutically acceptable salt thereof and is disclosed in European Patent Application No. EP560268, published Sep. 15, 1993, which is incorporated herein by reference.

BILA 1096 BS is

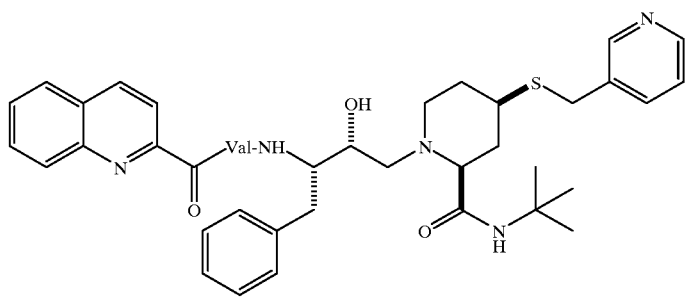

or a pharmaceutically acceptable salt thereof and is disclosed in European Patent Application No. EP560268, published Sep. 15, 1993, which is incorporated herein by reference.

BILA 2185 BS is

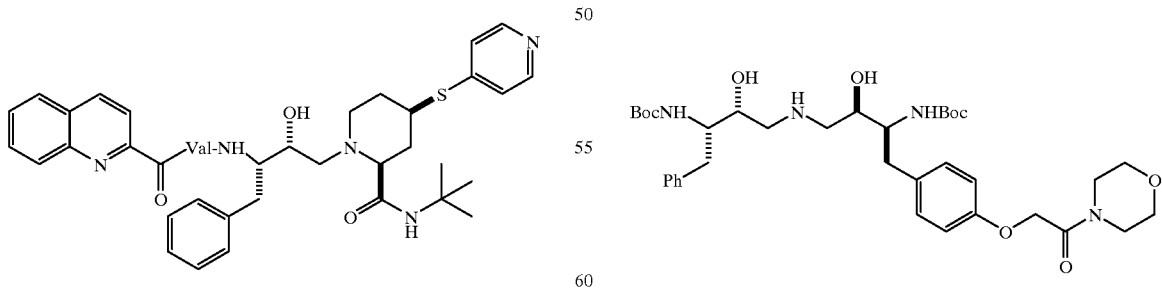

or a pharmaceutically acceptable salt thereof and is disclosed in European Patent Application No. EP560268, published Sep. 15, 1993, which is incorporated herein by reference.

BMS 186,318 is or a pharmaceutically acceptable salt thereof and is disclosed in European Patent Application No. EP580402, published Jan. 26, 1994, which is incorporated herein by reference.

LB71262 is

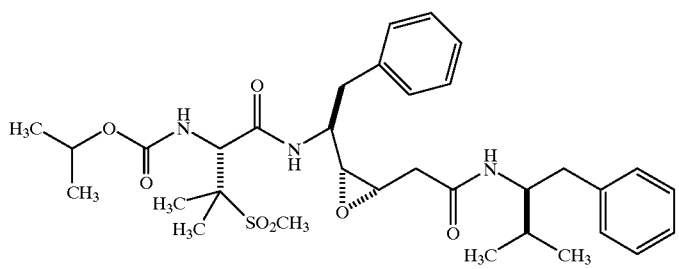

and is disclosed in European Patent Application No. EP687675, published Dec. 20, 1995, which is incorporated herein by reference.

SC-52151 is [1S-[1R*(R*),2S*]}-N¹[3-[[[(1,1-dimethylethyl)-amino]carbonyl](2-methylpropyl)amino]-2-hydroxy-1-(phenylmethyl)propyl]-2-[(2-quinolinylcarbonyl)amino]-butanediamide or a pharmaceutically acceptable salt thereof and is disclosed in PCT Patent Application No. WO92/08701, published May 29, 1992 and PCT Patent Application No. WO93/23368, published Nov. 25, 1993, both of which are incorporated herein by reference.

SC-629 (N,N-dimethylglycyl-N-(2-hyrdoxy-3-(((4-methoxyphenyl)sulphonyl)(2-methylpropyl)amino)-1-(phenylmethyl)propyl)-3-methyl-L-valinamide) is CGP 53437 is

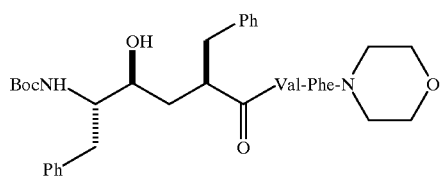

and is disclosed in European Patent Application No. EP532466, published Mar. 17, 1993, which is incorporated herein by reference.

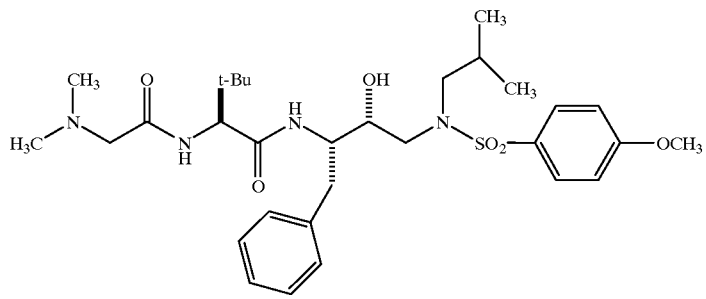

or a pharmaceutically acceptable salt thereof and is disclosed in PCT Patent Application No. WO095/06030, published Mar. 2, 1995, which is incorporated herein by reference.

KNI-272 is

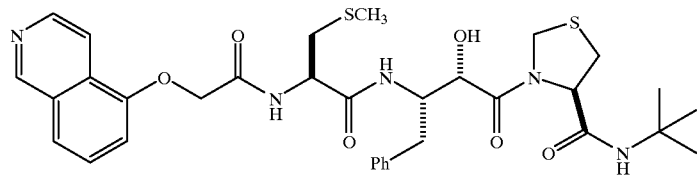

or a pharmaceutically acceptable salt thereof and is disclosed in European Patent Application No. EP574135, published Dec. 15, 1993, which is incorporated herein by reference.

CGP 57813 is

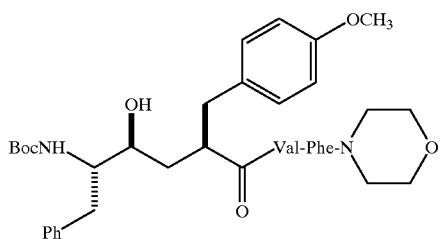

and is disclosed in European Patent Application No. EP618222, published Oct. 5, 1994, which is incorporated herein by reference.

U-103017 is

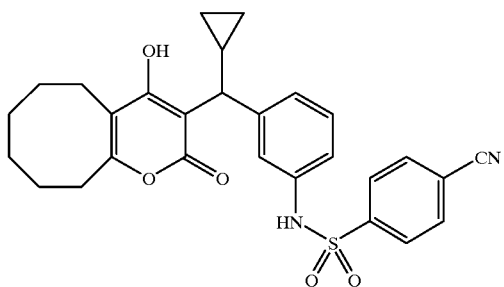

and is disclosed in PCT Patent Application No. WO94/418188, published Aug. 18, 1994, which is incorporated herein by reference.

The terms "S" and "R" configuration are as defined by the IUPAC 1974 Recommendations for Section E, Fundamental Stereochemistry, Pure Appl. Chem. (1976) 45, 13–30.

The term "Val" as used herein refers to valine. Unless otherwise noted, when "Val" is used herein it refers to the L-isomer. In general, the amino acid abbreviations used herein follow the IUPAC-IUB Joint Commission on Biochemical Nomenclature for amino acids and peptides (Eur. J. Biochem. 1984, 158, 9–31).

The ability of a compound to inhibit HIV protease can be demonstrated according to the methods disclosed in PCT Patent Application No. WO94/14436.

The ability of an HIV protease inhibitor to inhibit an HIV infection can be demonstrated according to the methods disclosed in PCT Patent Application No. WO94/14436.

Inhibition of Cytochrome P450

The ability of ritonavir to inhibit cytochrome P450 monooxygenase activity was tested with terfenadine as the probe substrate (Yun, et al., Drug Metabolism & Disposition, Vol. 21 403–407 (1993)). Ritonavir inhibited the terfenadine hydroxylase activity representing the most abundant form of cytochrome P450 (CYP3A4) present in human liver with an $IC_{50}$ of 0.25 $\mu M$.

Pharmacokinetic Improvement

The ability of ritonavir to improve the pharmacokinetics of a compound which is metabolized by cytochrome P450 monooxygenase can be demonstrated by the test method described below, wherein VX-478 is used as an example.

Rats (male, Sprague-Dawley derived, 0.3–0.45 kg) were fasted overnight prior to dosing, but were permitted water ad libitum. For combination dosing, a single solution containing both ritonavir and VX-478 (5 mg/ml each) was prepared in a vehicle of 20% ethanol:30% propylene glycol and D5W with an appropriate number of molar equivalents of methane sulfonic acid to assist in solubilization. Separate solutions of VX-478 and ritonavir were also prepared and these solutions were used to evaluate the pharmacokinetics of VX-478 and ritonavir when administered as a single agent in rats. The solutions, administered orally by gavage to a group of rats at a dose volume of 2 ml/kg, provided a 10 mg/kg dose of each compound. Blood samples were obtained from a tail vein of each rat 0.25, 0.5, 1, 1.5, 2, 3, 4, 6 and 8 hours after dosing. The plasma was separated from the red cells by centrifugation and frozen (–30° C.) until analysis. Concentrations of both ritonavir and VX-478 were determined simultaneously by reverse phase HPLC with low wavelength UV detection following liquid-liquid extraction of the plasma samples. The peak plasma concentration ($C_{max}$) and time to peak plasma concentration ($T_{max}$) for each rat were obtained directly from the plasma concentration data. The area under the curve was calculated by the trapezoidal method over the time course of the study. The plasma elimination half life was obtained from NONLIN84 or from a log-linear regression of the terminal plasma concentrations as a function of time after dosing. Each combination was evaluated in a group containing at least three rats; the values reported are averages for each group of animals. The data obtained from the combination was compared to data obtained from a separate group of rats which received a single, separate dose of the compound under evaluation.

Below in Table 1 are shown the results from the pharmacokinetic experiments with VX-478 and other HIV protease inhibitors in rats. The maximum plasma levels ($C_{max}$), time to maximum plasma level ($T_{max}$) and area under the plasma concentration curve (AUC) for an 8-hour sampling interval following dosing of the HIV protease inhibitor alone vs. dosing in combination with ritonavir are provided.

TABLE 1

| Compound | Cmax (mcg/ml) | Tmax (hr) | AUC(0–8 h) (mcg · hr/ml) |
|---|---|---|---|
| VX-478‡ | 1.61 | 0.42 | 1.69 |
| VX-478 (+ritonavir) | 2.88 | 1.5 | 13.50 |
| A-77003‡ | 0.07 | 0.25 | 0.025 |
| A-77003 (+ritonavir) | 0.96 | 0.67 | 1.39 |
| A-80987‡ | 2.42 | 0.25 | 1.45 |
| A-80987 (+ritonavir) | 4.47 | 1.7 | 25.74 |
| Saquinavir‡ | 0.08 | 0.18 | 0.029 |
| Saquinavir (+ritonavir) | 1.48 | 3.0 | 8.52 |
| MK-639‡ | 1.03 | 0.5 | 0.81 |
| MK-639 (+ritonavir) | 1.40 | 3.0 | 6.51 |
| AG1343‡ | 0.40 | 0.75 | 1.14 |
| AG1343 (+ritonavir) | 1.81 | 4.0 | 11.92 |

‡compound administered as a single agent

The ability of ritonavir to improve the pharmacokinetics of clarithromycin in humans was demonstrated according to the method described below.

Clarithromycin (500 mg/BIAXIN® tablet every 12 hours) and a combination of ritonavir (200 mg of liquid formulation every 8 hours) and clarithromycin (500 mg every 12 hours) were administered to groups of 4 healthy human volunteers. Blood samples were collected on day four of dosing for HPLC determination of plasma concentrations of clarithromycin.

Below in Table 2 are shown the results from the pharmacokinetic experiments with clarithromycin in humans. The mean maximum plasma levels ($C_{max}$) and area under the plasma concentration curve (AUC) calculated using noncompartmental methods for the 0–24 hour time interval on day four of dosing of clarithromycin alone vs. dosing in combination with ritonavir are provided.

TABLE 2

| Compound | Cmax (mcg/ml) | AUC(0–24 h) (mcg · hr/ml) |
|---|---|---|
| clarithromycin‡ | 3.93 | 49.04 |
| clarithromycin (+ritonavir) | 5.13 | 86.88 |

‡compound administered as a single agent

The therapeutic agents of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

The administration of ritonavir and a compound which is metabolized by cytochrome P450 monooxygenase is useful for improving in humans the pharmacokinetics of the compound which is metabolized by cytochrome P450 monooxygenase.

In particular, the administration of ritonavir and an HIV protease inhibitor which is metabolized by cytochrome P450 monooxygenase is useful for improving in humans the pharmacokinetics of the HIV protease inhibitor which is metabolized by cytochrome P450 monooxygenase.

The combination of ritonavir and an HIV protease inhibitor which is metabolized by cytochrome P450 monooxygenase is also useful for inhibiting a retroviral protease, in particular HIV protease, in vitro or in vivo (especially in mammals and in particular in humans). This combination of therapeutic agents is also useful for the inhibition of retroviruses in vivo, especially human immunodeficiency virus (HIV). This combination of therapeutic agents is also useful for the treatment or prophylaxis of diseases caused by retroviruses, especially acquired immune deficiency syndrome or an HIV infection, in a human or other mammal.

The total daily dose of ritonavir to be administered to a human or other mammal host in single or divided doses may be in amounts, for example, from 0.001 to 300 mg/kg body weight daily and more usually 0.1 to 50 mg/kg and even more usually 0.1 to 25 mg/kg. Dosage unit compositions may contain such amounts of submultiples thereof to make up the daily dose.

The total daily dose of the drug which is metabolized by cytochrome P450 monooxygenase to be administered to a human or other mammal is well known and can be readily determined by one of ordinary skill in the art. Dosage unit compositions may contain such amounts of submultiples thereof to make up the daily dose.

The amount of active ingredient that may be combined with the carrier materials to produce a single dosage form of each drug, individually or in combination, will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The combination of therapeutic agents of the present invention (as individual compositions or as a single composition) may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The combination of therapeutic agents of the present invention (as individual compositions or as a single composition) can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically aceptable and metabolizable lipid capabale of forming liposomes can be used. The present compositions in liposome form can contain, in addition to the compound of the present invention, stabilizers, preservatives, excipients, and the like. The preferred lipids are the phospholipids and phosphatidyl cholines (lecithins), both natureal and synthetic.

Methods to form liposomes are known in the art. See, for example, Prescott, Ed., *Methods in Cell Biology*, Volume XIV, Academic Press, New York, N.Y. (1976), p. 33 et seq.

Preferred dosage forms for ritonavir include (a) a liquid dosage form for oral administration as disclosed in U.S. Ser. No. 08/283, 239, filed Jul. 29, 1994 (now U.S. Pat. No. 5,484,801, issued Jan. 16, 1996), which is incorporated herein by reference, (b) an encapsulated solid or semi-solid dosage form as disclosed in PCT Patent Application No. WO95/07696, published Mar. 23, 1995 and U.S. Ser. No. 08/402,690, filed March 13, 1995, both of which are incorporated herein by reference and (c) an encapsulated solid dosage form as disclosed in PCT Patent Application No. WO95/09614, published Apr. 13, 1995, which is incorporated herein by reference.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A method for improving the pharmacokinetics of a drug which is metabolized by cytochrome P450 monooxygenase comprising administering to a human in need of such treatment a therapeutically effective amount of a combination of said drug or a pharmaceutically acceptable salt thereof and ritonavir or a pharmaceutically acceptable salt thereof.

2. The method of claim 1 wherein the drug which is metabolized by cytochrome P450 monooxygenase is selected from the group consisting of cyclosporine, FK-506, rapamycin, taxol , taxotere, clarithromycin, A-77003, A-80987, MK-639, saquinavir, VX-478, AG1343, DMP-323, XM-450, BILA 2011 BS, BILA 1096 BS, BILA 2185 BS, BMS 186,318, LB71262, SC-52151, SC-629, KNI-272, CGP 53437, CGP 57813 and U-103017.

3. The method of claim 1 wherein the drug which is metabolized by cytochrome P450 monooxygenase is selected from the group consisting of A-77003, A-80987, MK-639, saquinavir, VX-478, AG1343, DMP-323, XM-450, BILA 2011 BS, BILA 1096 BS, BILA 2185 BS, BMS 186,318, LB71262, SC-52151, SC-629, KNI-272, CGP 53437, CGP 57813 and U-103017.

4. The method of claim 1 wherein the drug which is metabolized by cytochrome P450 monooxygenase is selected from the group consisting of A-77003, A-80987, MK-639, saquinavir, VX-478 and AG1343.

5. The method of claim 1 wherein the drug which is metabolized by cytochrome P450 monooxygenase is saquinavir.

6. The method of claim 1 wherein the drug which is metabolized by cytochrome P450 monooxygenase is VX-478.

7. The method of claim 1 wherein the drug which is metabolized by cytochrome P450 monooxygenase is MK-639.

8. The method of claim 1 wherein the drug which is metabolized by cytochrome P450 monooxygenase is AG1343.

9. A method for increasing human blood levels of a drug which is metabolized by cytochrome P450 monooxygenase comprising administering to a human in need of such treatment a therapeutically effective amount of a combination of said drug or a pharmaceutically acceptable salt thereof and ritonavir or a pharmaceutically acceptable salt thereof.

10. The method of claim 9 wherein the drug which is metabolized by cytochrome P450 monooxygenase is selected from the group consisting of cyclosporine, FK-506, rapamycin, taxol , taxotere, clarithromycin, A-77003, A-80987, MK-639, saquinavir, VX-478, AG1343, DMP-323, XM-450, BILA 2011 BS, BILA 1096 BS, BILA 2185 BS, BMS 186,318, LB71262, SC-52151, SC-629, KNI-272, CGP 53437, CGP 57813 and U-103017.

11. The method of claim 9 wherein the drug which is metabolized by cytochrome P450 monooxygenase is selected from the group consisting of A-77003, A-80987, MK-639, saquinavir, VX-478, AG1343, DMP-323, XM-450, BILA 2011 BS, BILA 1096 BS, BILA 2185 BS, BMS 186,318, LB71262, SC-52151, SC-629, KNI-272, CGP 53437, CGP 57813 and U-103017.

12. The method of claim 9 wherein the drug which is metabolized by cytochrome P450 monooxygenase is selected from the group consisting of A-77003, A-80987, MK-639, saquinavir, VX-478 and AG1343.

13. The method of claim 9 wherein the drug which is metabolized by cytochrome P450 monooxygenase is saquinavir.

14. The method of claim 9 wherein the drug which is metabolized by cytochrome P450 monooxygenase is VX-478.

15. The method of claim 9 wherein the drug which is metabolized by cytochrome P450 monooxygenase is MK-639.

16. The method of claim 9 wherein the drug which is metabolized by cytochrome P450 monooxygenase is AG1343.

17. A method for inhibiting cytochrome P450 monooxygenase comprising administering to a human in need thereof an amount of ritonavir or a pharmaceutically acceptable salt thereof effective to inhibit cytochrome P450 monooxygenase.

18. A method for inhibiting cytochrome P450 monooxygenase comprising contacting the cytochrome P450 monooxygenase with an amount of ritonavir or a pharmaceutically acceptable salt thereof effective to inhibit cytochrome P450 monooxygenase.

* * * * *

UNITED STATES PATENT AND TRADEMARK OFFICE
CERTIFICATE OF CORRECTION

PATENT NO. : 6,037,157
DATED : March 14, 2000
INVENTOR(S) : Daniel W. Norbeck et al Page 1 of 2

It is certified that error appears in the above-indentified patent and that said Letters Patent is hereby corrected as shown below:

Col. 1, line 23
replace "immumodeficiency"
with --immunodeficiency--.
Col. 4, line 7
replace " 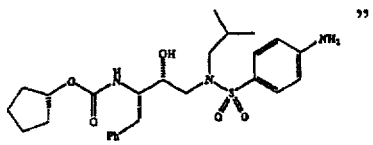 "

with -- 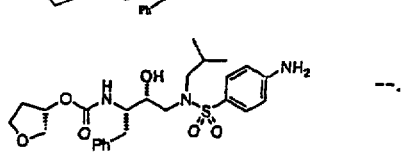 --.

UNITED STATES PATENT AND TRADEMARK OFFICE
CERTIFICATE OF CORRECTION

PATENT NO. : 6,037,157
DATED : March 14, 2000
INVENTOR(S) : Daniel W. Norbeck et al It is certified that error appears in the above-indentified patent and that said Letters Patent is hereby corrected as shown below:

Col. 5, line 1
    replace "BILA 2011 is"
    with --BILA 2011 BS is--.
    Col. 10, line 13
    replace "(-30°C.)"
    with -- (-30°C)--.
    Col. 13, line 18
    replace "natureal"
    with --natural--.

Signed and Sealed this

Thirteenth Day of March, 2001

Attest:

NICHOLAS P. GODICI

Attesting Officer     Acting Director of the United States Patent and Trademark Office

(12) EX PARTE REEXAMINATION CERTIFICATE (9675th)
United States Patent
Norbeck et al.

(10) Number: US 6,037,157 C1
(45) Certificate Issued: May 24, 2013

(54) METHOD FOR IMPROVING PHARMACOKINETICS

(75) Inventors: Daniel W. Norbeck, Crystal Lake, IL (US); Dale J. Kempf, Libertyville, IL (US); John M. Leonard, Lake Bluff, IL (US); Richard J. Bertz, Kenosha, WI (US)

(73) Assignee: Abbott Laboratories, Abbott Park, IL (US)

Reexamination Request:
No. 90/009,810, Aug. 25, 2010

Reexamination Certificate for:
Patent No.: 6,037,157
Issued: Mar. 14, 2000
Appl. No.: 08/687,774
Filed: Jun. 26, 1996

Certificate of Correction issued Mar. 13, 2001

Related U.S. Application Data

(60) Provisional application No. 60/000,654, filed on Jun. 29, 1995, provisional application No. 60/003,849, filed on Sep. 15, 1995.

(51) Int. Cl.
*A61K 31/337* (2006.01)
*A61K 31/341* (2006.01)
*A61K 31/395* (2006.01)
*A61K 31/426* (2006.01)
*A61K 31/44* (2006.01)
*A61K 31/453* (2006.01)
*A61K 31/498* (2006.01)
*A61K 31/7048* (2006.01)
*A61K 38/05* (2006.01)
*A61K 38/06* (2006.01)
*A61K 38/55* (2006.01)
*A61K 31/4523* (2006.01)
*A61K 31/7042* (2006.01)
*C07D 277/28* (2006.01)

(52) U.S. Cl.
USPC ............ 435/184; 514/365; 548/204; 548/205

(58) Field of Classification Search
USPC .......................................................... 435/184
See application file for complete search history.

(56) References Cited

To view the complete listing of prior art documents cited during the proceeding for Reexamination Control Number 90/009,810, please refer to the USPTO's public Patent Application Information Retrieval (PAIR) system under the Display References tab.

*Primary Examiner* — Bruce Campell

(57) ABSTRACT

A method is disclosed for improving the pharmacokinetics of a drug which is metabolized by cytochrome P450 monooxygenase.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 5, 13, 17 and 18 are cancelled.

Claims 1-4, 6-12 and 14-16 are determined to be patentable as amended.

New claims 19-46 are added and determined to be patentable.

1. A method for improving the pharmacokinetics of a drug which is metabolized by cytochrome P450 monooxygenase comprising administering to a human in need of such treatment a therapeutically effective amount of a combination of said drug or a pharmaceutically acceptable salt thereof and ritonavir or a pharmaceutically acceptable salt thereof, *wherein the drug which is metabolized by cytochrome P450 monooxygenase is not FK-506, clarithromycin, saquinavir, SC-52151, or KNI-272.*

2. The method of claim 1 wherein the drug which is metabolized by cytochrome P450 monooxygenase is selected from the group consisting of cyclosporine, [FK-506,] rapamycin, taxol, taxotere, [clarithromycin,] A-77003, A-80987, MK-639, [saquinavir,] VX-478, AG1343, DMP-323, XM-450, BILA 2011 BS, BILA 1096 BS, BILA 2185 BS, BMS 186,318, LB71262, [SC-52151,] SC-629, [KNI-272,] CGP 53437, CGP 57813 and U-103017.

3. The method of claim 1 wherein the drug which is metabolized by cytochrome P450 monooxygenase is selected from the group consisting of A-77003, A-80987, MK-639, [saquinavir,] VX-478, AG1343, DMP-323, XM-450, BILA 2011 BS, BILA 1096 BS, BILA 2185 BS, BMS 186,318, LB71262, [SC-52151,] SC-629, [KNI-272,] CGP 53437, CGP 57813 and U-103017.

4. The method of claim 1 wherein the drug which is metabolized by cytochrome P450 monooxygenase is selected from the group consisting of A-77003, A-80987, MK-639, [saquinavir,] VX-478 and AG1343.

6. [The method of claim 1] *A method for improving the pharmacokinetics of a drug which is metabolized by cytochrome P450 monooxygenase comprising administering to a human in need of such treatment a therapeutically effective amount of a combination of said drug or a pharmaceutically acceptable salt thereof and ritonavir or a pharmaceutically acceptable salt thereof,* wherein the drug which is metabolized by cytochrome P450 monooxygenase is VX-478.

7. [The method of claim 1] *A method for improving the pharmacokinetics of a drug which is metabolized by cytochrome P450 monooxygenase comprising administering to a human in need of such treatment a therapeutically effective amount of a combination of said drug or a pharmaceutically acceptable salt thereof and ritonavir or a pharmaceutically acceptable salt thereof,* wherein the drug which is metabolized by cytochrome P450 monooxygenase is MK-639.

8. [The method of claim 1] *A method for improving the pharmacokinetics of a drug which is metabolized by cytochrome P450 monooxygenase comprising administering to a human in need of such treatment a therapeutically effective amount of a combination of said drug or a pharmaceutically acceptable salt thereof and ritonavir or a pharmaceutically acceptable salt thereof,* wherein the drug which is metabolized by cytochrome P450 monooxygenase is AG1343.

9. A method for increasing human blood levels of a drug which is metabolized by cytochrome P450 monooxygenase comprising administering to a human in need of such treatment a therapeutically effective amount of a combination of said drug or a pharmaceutically acceptable salt thereof and ritonavir or a pharmaceutically acceptable salt thereof,
*wherein the drug which is metabolized by cytochrome P450 monooxygenase is not FK-506, clarithromycin, saquinavir, SC-52151, or KNI-272.*

10. The method of claim 9 wherein the drug which is metabolized by cytochrome P450 monooxygenase is selected from the group consisting of cyclosporine, [FK-506,] rapamycin, taxol, taxotere, [clarithromycin,] A-77003, A-80987, MK-639, [saquinavir,] VX-478, AG1343, DMP-323, XM-450, BILA 2011 BS, BILA 1096 BS, BILA 2185 BS, BMS 186,318, LB71262, [SC-52151,] SC-629, [KNI-272,] CGP 53437, CGP 57813 and U-103017.

11. The method of claim 9 wherein the drug which is metabolized by cytochrome P450 monooxygenase is selected from the group consisting of A-77003, A-80987, MK-639, [saquinavir,] VX-478, AG1343, DMP-323, XM-450, BILA 2011 BS, BILA 1096 BS, BILA 2185 BS, BMS 186,318, LB71262, [SC-52151,] SC-629, [KNI-272,] CGP 53437, CGP 57813 and U-103017.

12. The method of claim 9 wherein the drug which is metabolized by cytochrome P450 monooxygenase is selected from the group consisting of A-77003, A-80987, MK-639, [saquinavir,] VX-478 and AG1343.

14. [The method of claim 9] *A method for increasing human blood levels of a drug which is metabolized by cytochrome P450 monooxygenase comprising administering to a human in need of such treatment a therapeutically effective amount of a combination of said drug or a pharmaceutically acceptable salt thereof and ritonavir or a pharmaceutically acceptable salt thereof,* wherein the drug which is metabolized by cytochrome P450 monooxygenase is VX-478.

15. [The method of claim 9] *A method for increasing human blood levels of a drug which is metabolized by cytochrome P450 monooxygenase comprising administering to a human in need of such treatment a therapeutically effective amount of a combination of said drug or a pharmaceutically acceptable salt thereof and ritonavir or a pharmaceutically acceptable salt thereof,* wherein the drug which is metabolized by cytochrome P450 monooxygenase is MK-639.

16. [The method of claim 9] *A method for increasing human blood levels of a drug which is metabolized by cytochrome P450 monooxygenase comprising administering to a human in need of such treatment a therapeutically effective amount of a combination of said drug or a pharmaceutically acceptable salt thereof and ritonavir or a pharmaceutically acceptable salt thereof,* wherein the drug which is metabolized by cytochrome P450 monooxygenase is AG1343.

*19. The method of claim 1, wherein said P450 monooxygenase is cytochrome P450 monooxygenase 3A4.*

*20. The method of claim 1, wherein the drug which is metabolized by cytochrome P450 monooxygenase is a HIV protease inhibitor.*

*21. The method of claim 20, wherein said cytochrome P450 monooxygenase is cytochrome P450 monooxygenase 3A4.*

22. The method of claim 1 wherein the drug which is metabolized by cytochrome P450 monooxygenase is not a HIV protease inhibitor.

23. The method of claim 22, wherein said cytochrome P450 monooxygenase is cytochrome P450 monooxygenase 3A4.

24. The method of claim 1 wherein said drug is administered in such an amount that would lead to less favorable pharmacokinetics if administered without ritonavir.

25. The method of claim 24, wherein said cytochrome P450 monooxygenase is cytochrome P450 monooxygenase 3A4.

26. The method of claim 9, wherein said P450 monooxygenase is cytochrome P450 monooxygenase 3A4.

27. The method of claim 9, wherein the drug which is metabolized by cytochrome P450 monooxygenase is a HIV protease inhibitor.

28. The method of claim 27, wherein said cytochrome P450 monooxygenase is cytochrome P450 monooxygenase 3A4.

29. The method of claim 9 wherein the drug which is metabolized by cytochrome P450 monooxygenase is not a HIV protease inhibitor.

30. The method of claim 29, wherein said cytochrome P450 monooxygenase is cytochrome P450 monooxygenase 3A4.

31. The method of claim 9 wherein said drug is administered in such an amount that would lead to less favorable pharmacokinetics if administered without ritonavir.

32. The method of claim 31, wherein said cytochrome P450 monooxygenase is cytochrome P450 monooxygenase 3A4.

33. The method of claim 1, wherein the therapeutically effective amount of ritonavir is about 200 mg per dose.

34. A method for improving the pharmacokinetics of a drug which is metabolized by cytochrome P450 monooxygenase comprising administering to a human in need of such treatment a therapeutically effective amount of a combination of said drug or a pharmaceutically acceptable salt thereof and ritonavir or a pharmaceutically acceptable salt thereof, wherein the drug which is metabolized by cytochrome P450 monooxygenase or the pharmaceutically acceptable salt thereof is administered at less frequent or lower doses than that at which the drug which is metabolized by cytochrome P450 monooxygenase or the pharmaceutically acceptable salt thereof is effective when administered without ritonavir.

35. The method of claim 34, wherein said P450 monooxygenase is cytochrome P450 monooxygenase 3A4.

36. The method of claim 34, wherein the drug which is metabolized by cytochrome P450 monooxygenase or the pharmaceutically acceptable salt thereof is a HIV protease inhibitor.

37. The method of claim 36, wherein said cytochrome P450 monooxygenase is cytochrome P450 monooxygenase 3A4.

38. The method of claim 34, wherein the drug which is metabolized by cytochrome P450 monooxygenase or the pharmaceutically acceptable salt thereof is not a HIV protease inhibitor.

39. The method of claim 38, wherein said cytochrome P450 monooxygenase is cytochrome P450 monooxygenase 3A4.

40. A method for increasing human blood levels of a drug which is metabolized by cytochrome P450 monooxygenase comprising administering to a human in need of such treatment a therapeutically effective amount of a combination of said drug or a pharmaceutically acceptable salt thereof and ritonavir or a pharmaceutically acceptable salt thereof, wherein the drug which is metabolized by cytochrome P450 monooxygenase or the pharmaceutically acceptable salt thereof is administered at less frequent or lower doses than that at which said drug or the salt thereof is effective when administered without ritonavir.

41. The method of claim 40, wherein said P450 monooxygenase is cytochrome P450 monooxygenase 3A4.

42. The method of claim 40, wherein the drug which is metabolized by cytochrome P450 monooxygenase or the pharmaceutically acceptable salt thereof is a HIV protease inhibitor.

43. The method of claim 42, wherein said cytochrome P450 monooxygenase is cytochrome P450 monooxygenase 3A4.

44. The method of claim 40, wherein the drug which is metabolized by cytochrome P450 monooxygenase or the pharmaceutically acceptable salt thereof is not a HIV protease inhibitor.

45. The method of claim 44, wherein said cytochrome P450 monooxygenase is cytochrome P450 monooxygenase 3A4.

46. A method for improving the pharmacokinetics of a drug which is metabolized by cytochrome P450 monooxygenase comprising administering to a human in need of such treatment a therapeutically effective amount of a combination of said drug or a pharmaceutically acceptable salt thereof and ritonavir or a pharmaceutically acceptable salt thereof, wherein the ritonavir or the pharmaceutically acceptable salt thereof is administered in a dosage less than the dosage at which ritonavir or the pharmaceutically acceptable salt thereof is independently effective to treat HIV.

* * * * *